US008083801B2

(12) United States Patent
Chen

(10) Patent No.: US 8,083,801 B2

(45) Date of Patent: Dec. 27, 2011

(54) SINUS MEMBRANE PERFORATION CORRECTIVE PROCEDURE

(76) Inventor: Chun-Leon Chen, Las Vegas, NV (US)

( * ) Notice: Subject to any disclaimer, the term of this patent is extended or adjusted under 35 U.S.C. 154(b) by 237 days.

(21) Appl. No.: 12/487,505

(22) Filed: Jun. 18, 2009

(65) Prior Publication Data

US 2010/0203473 A1 Aug. 12, 2010

Related U.S. Application Data

(63) Continuation-in-part of application No. 12/366,815, filed on Feb. 6, 2009.

(51) Int. Cl.
*A61F 2/02* (2006.01)

(52) U.S. Cl. .................................... 623/17.17; 128/898

(58) Field of Classification Search .................. 433/114, 433/141, 201.1, 215; 606/8, 84, 86 R, 92, 606/93, 139, 151, 153, 199, 213, 215, 216, 606/232, 233; 623/17.17, 17.18, 23.61, 23.76, 623/902, 908; 128/898
See application file for complete search history.

(56) References Cited

U.S. PATENT DOCUMENTS 4,521,192 A * 6/1985 Linkow ........................ 433/173
6,821,121 B2 * 11/2004 Rosen .......................... 433/142
7,097,650 B2 * 8/2006 Weller et al. ................. 606/153
7,125,253 B2 10/2006 Kitamura et al.
7,288,105 B2 * 10/2007 Oman et al. ................. 606/215
2003/0211443 A1 * 11/2003 Magee, III .................... 433/141
2004/0092973 A1 * 5/2004 Chanduszko et al. ........ 606/151
2006/0287732 A1 * 12/2006 Pezeshkian ................ 623/17.17
2008/0161834 A1 * 7/2008 Yamada ........................ 128/898
2009/0054934 A1 * 2/2009 Beyar et al. .................. 523/116

* cited by examiner

*Primary Examiner* — Brian E. Pellegrino
(74) *Attorney, Agent, or Firm* — Guice Patents PLLC

(57) ABSTRACT

A sinus correction method is disclosed. For example, one embodiment comprises making an incision in gingival tissue surrounding a sinus membrane perforation, dissecting the gingival tissue from cortical bone, dissecting sinus membrane adjacent to the gingival tissue from the cortical bone, overlapping the sinus membrane and adjacent gingival tissue from two sides of the sinus membrane perforation, connecting the overlapping sinus membrane and adjacent gingival tissue from two sides of the sinus membrane perforation, and applying a bone graft composition adjacent to the overlapping sinus membrane, the bone graft composition to form bone connected with cortical bone sufficient to place a dental implant.

7 Claims, 4 Drawing Sheets

44 4 42 45 (A) 41
4 42 44 43 (B) 41 43
4 41 21 (C) 43 8
4 41 8 21 (D)
4 41 8 43 21 (E) 41
4 46 (F)
4 5 31 (G)
4 5 6 44 (H) 31

SINUS MEMBRANE PERFORATION CORRECTIVE PROCEDURE

CROSS REFERENCE TO RELATED APPLICATIONS

The present application is a continuation-in-part of U.S. patent application Ser. No. 12/366,815, filed Feb. 6, 2009, entitled "DENTAL INSTRUMENT FOR LIFTING SINUS MEMBRANE AND APPLYING BONE POWDER", the entire contents of which are incorporated herein by reference.

BACKGROUND

The present invention relates to dental procedures and equipment and more particularly, to a procedure and equipment for lifting a sinus membrane and applying bone graft particulate to a maxillary sinus.

Dental implants have become a preferred solution for resolving the partial or total edentulism of the jaw. Dental implants are made of titanium metal that is of a highly biocompatible material, and does not disintegrate into bio-toxicity while being installed in human bodies. Therefore, the dental implants, with proper surgical procedures, at approximately a 96% success rate, can provide improved function, aesthetics, and prevention of bone loss, etc.

In general, a dental implant is a substitute for a lost natural tooth, or a dental operation, in which a screw shape fixture is secured to the jawbone and fused with the jawbone for a predetermined period of time, and then an abutment, i.e. a coupling part, and a prosthesis such as an artificial tooth crown are fixed to the fixture so as to restore the original function of a tooth.

A false tooth or crown is provided with a hole, known as a chimney, there through, and a non-round recess in its base that corresponds in shape to the protruding non-round cross-section of the abutment. Thereby, the crown can be joined to the abutment with a self-aligning connection that prevents relative rotation between them. A screw, passed into the chimney opening, engages the tapped hole in the abutment so as to hold the crown axially to the abutment. Thus, the crown cannot rotate about the abutment because it is fixed into the special contours on the exposed abutment end, and the crown cannot pull away from the abutment when the screw has been tightened in place. Finally, the chimney above the screw is filled with a composite filler material that hardens and is shaped as part of the crown, to look like a natural tooth.

The inventor of the present invention disclosed a rapid dental implant implantation operation for allowing rapid implantation of a dental implant. To facilitate performance of this rapid dental implant implantation operation, the inventor created a number of dental instruments including U.S. application Ser. No. 12/357,046, entitled "Improved implant root for tooth implanting"; U.S. application Ser. No. 12/265,854, entitled "Drill for rapid dental implant"; Taiwan Utility M313502, entitled "Adjustable double blade handle unit"; Taiwan Utility M313504, entitled "Hydraulic pressure type nasal sinus membrane separator"; U.S. application Ser. No. 12/265,012, entitled "Vibrational filling device implanting tooth bone powder"; Taiwan Utility M313506, entitled "Toolset for raising height of nasal sinus."

Sinus lift treatment may be a technique used in a rapid dental implant implantation operation, wherein a hole is made in cortical bone and the sinus and to extend the hole to the bottom side of the sinus membrane. Further, in the related prior art designs of "Hydraulic pressure type nasal sinus membrane separator" of M313504, and "Tool set for raising height of nasal sinus" of M313506, a hydraulic sinus membrane separator is disclosed for use to separate the sinus membrane. However, the aforesaid hydraulic sinus membrane separator is simply for use to separate the sinus membrane from the cortical bone and may require additional tools for applying bone graft to the inside of the nasal sinus.

Unfortunately, during a sinus lift procedure, if a drill, a condenser, or other equipment slips, the sinus membrane may become damaged or even perforated. A sinus membrane may also be damaged during a tooth extraction or other dental procedures. Further, various degrees of damage to a sinus membrane may result during any type sinus lift, including a lateral window technique, a ridge technique, etc. Additionally, there is a considerable range of potential injuries to sinus membranes and each may require a specific corrective procedure, equipment, compositions of bone protein, etc.

SUMMARY

Accordingly, various embodiments for sinus correction, equipment, and compositions of matter are described below in the Detailed Description. For example, one embodiment comprises making an incision in gingival tissue surrounding a sinus membrane perforation, dissecting the gingival tissue from cortical bone, dissecting sinus membrane adjacent to the gingival tissue from the cortical bone, overlapping the sinus membrane and adjacent gingival tissue from two sides of the sinus membrane perforation, connecting the overlapping sinus membrane and adjacent gingival tissue from two sides of the sinus membrane perforation, and applying a bone graft composition adjacent to the overlapping sinus membrane, the bone graft composition to form bone connected with cortical bone sufficient to place a dental implant.

This Summary is provided to introduce concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

The following detailed description describes embodiments related to a sinus correction technique and related equipment and composition of matter. In an illustrative example, a sinus membrane perforation may be corrected by dissecting gingival tissue around the perforation, overlapping the gingival tissue and adjacent sinus membrane over the perforation, suturing the gingival tissue together and packing one or more bone graft compositions against the sutured gingival tissue and sinus membrane. In this way, the nasal cavity can be sealed off behind sinus membrane and a dental implantation may be performed on the bone graft composition when it forms bone connected with the existing cortical bone.

Figure 1:
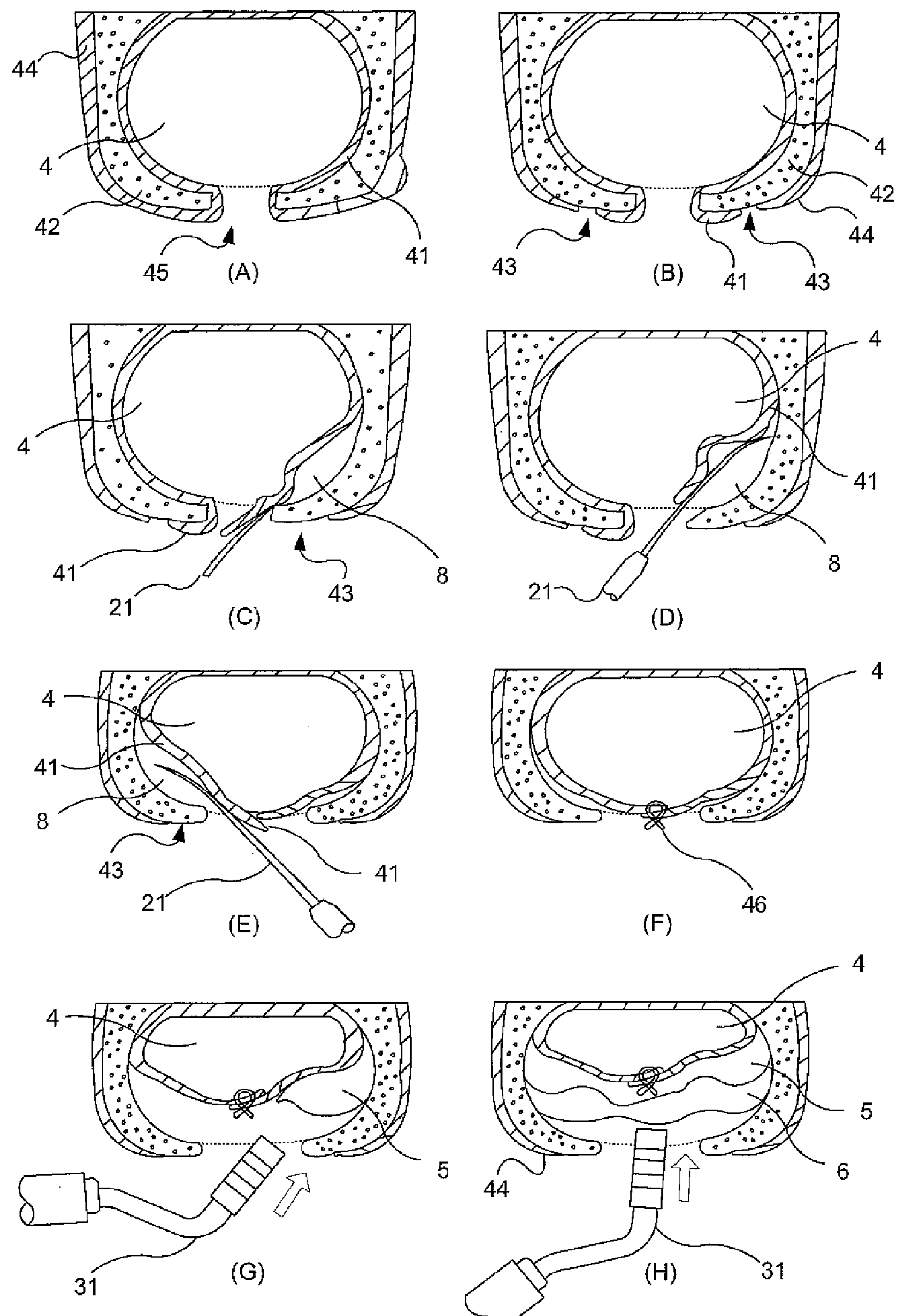
FIG. 1 is a series of drawings, showing application of a dental instrument and bone graft in a sinus lift treatment.

FIG. 1 illustrates a sinus operation before a dental implantation. FIG. 1A is a sectional view of the maxillary sinus 4 before a sinus operation where the cortical bone 42 of the sinus 4 is covered by sinus membrane 41 and gingival tissue 44. FIG. 1A also illustrated a perforation 45 exposing the sinus 4. FIG. 1B illustrates two cuts 43 being made on the gingival tissue 44 to facilitate performance of a sinus-lift treatment.

FIG. 1C illustrates the use of a dental instrument 1 for lifting a sinus membrane and applying bone graft. In particular, FIG. 1C illustrates a smoothly curved end portion 21 of a sinus membrane lifting tip 2 of dental instrument 1 being inserted into one cut 43 to dissect a part of the sinus membrane 41 from the cortical bone 42 in the maxillary sinus 4. Dental instrument 1 will be described in more detail below with reference to FIG. 2. Referring back to FIG. 1, maxillary sinus 4 may include the original nasal sinus, or sinus cavity space when no perforation is present, and also sinus membrane space 8 between the dissected sinus membrane and cortical bone 42. Further, the curved end portion 21 can be used to overlap the dissected sinus membrane 41 over the perforation 45.

The presently described embodiment illustrates using a dental instrument for lifting a sinus membrane and applying bone graft, however other embodiments are not so limited. For example, one or more dental instruments may also be used according to principles of this disclosure to dissect sinus membrane and/or overlap the sinus membrane and gingival tissue over a perforation 45.

Continuing with FIG. 1, FIG. 1D illustrates the smoothly curved end portion 21 of the sinus membrane lifting tip 2 inserted further into the one cut 43 to lift the sinus membrane 41 from the cortical bone 42 and increase the size of sinus membrane space 8. FIG. 1E illustrates the smoothly curved end portion 21 of the sinus membrane lifting tip 2 inserted into the other cut 43 to separate the other part of the sinus membrane 41 from the cortical bone 42 of the maxillary sinus 4 and to lift the sinus membrane 41. In this way, different portions of sinus membrane 41 may be dissected from the cortical bone 42 and another sinus membrane space 8 may be created. This dissection and overlapping procedure can be continued around a portion or all of the sinus membrane surrounding perforation 45. Further, FIG. 1E illustrates overlapping a second portion of sinus membrane 41 over the perforation and overlapping a first portion of the sinus membrane that was dissected in FIG. 1C.

FIG. 1F illustrates the two lifted parts of the sinus membrane 41 being connected together. In some embodiments multiple portions of sinus membrane 41 may be sutured together; however other embodiments may connect with tissue with other approaches and still be within the principles of this disclosure. With the sinus membrane overlapping the perforation and being sutured together, the maxillary sinus 4 is again an enclosed maxillary sinus cavity space.

FIGS. 1G and 1H illustrate a peripherally grooved end portion 31 of a bone graft applicator tip 3 on dental instrument 1 being used to pick up on bone graft composition 5 and insert the bone graft composition 5 into the space in the maxillary sinus 4. In some embodiments, bone graft composition 5 may be a spongy bone matrix composition in order to reduce a chance of damaging sinus membrane 41. Additionally, more than one type of bone graft composition may be used. For example, in FIG. 1H, a spongy bone matrix composition 5 is first placed next to the overlapped and sutured sinus membrane and gingival tissue and a particulate bone graft composition 6 is then packed in adjacent to the spongy bone matrix composition 5.

Figure 2:
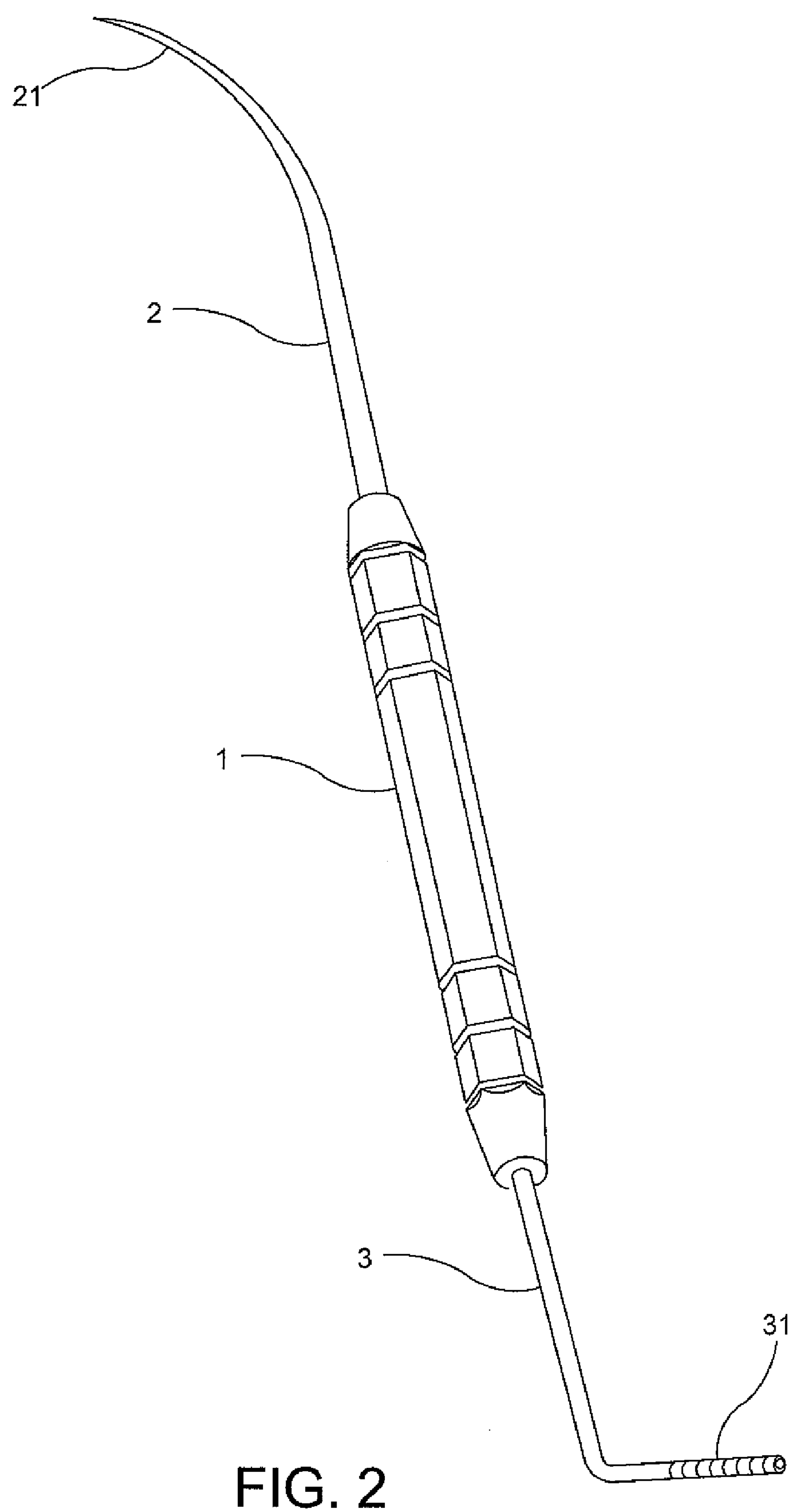
FIG. 2 is a perspective view of a dental instrument for lifting a sinus membrane and applying bone graft.

Referring to FIG. 2, a dental instrument for lifting a sinus membrane and applying a bone graft in accordance is shown comprising a handle 1, a sinus membrane lifting tip 2, and a bone graft condenser tip 3. In this embodiment, handle 1 is a rod member configured for the grasping of a dentist with one hand. The sinus membrane lifting tip 2 may be a narrow elongated member extended from one end of handle 1 and having a diameter of about 2 mm and a smoothly curved end portion 21 suitable for insertion into the maxillary sinus 4 to lift the sinus membrane 41 as described with reference to FIG. 1. The bone graft condenser tip 3 may be a substantially L-shaped rod member extended from the other end of the handle 1 and having a peripherally grooved end portion 31 for applying bone graft 5 to the inside of the maxillary sinus 4 as described herein. In some embodiments, sinus membrane lifting tip 2 and bone graft condenser tip 3 may be coated with a layer of titanium coating.

Figure 3:
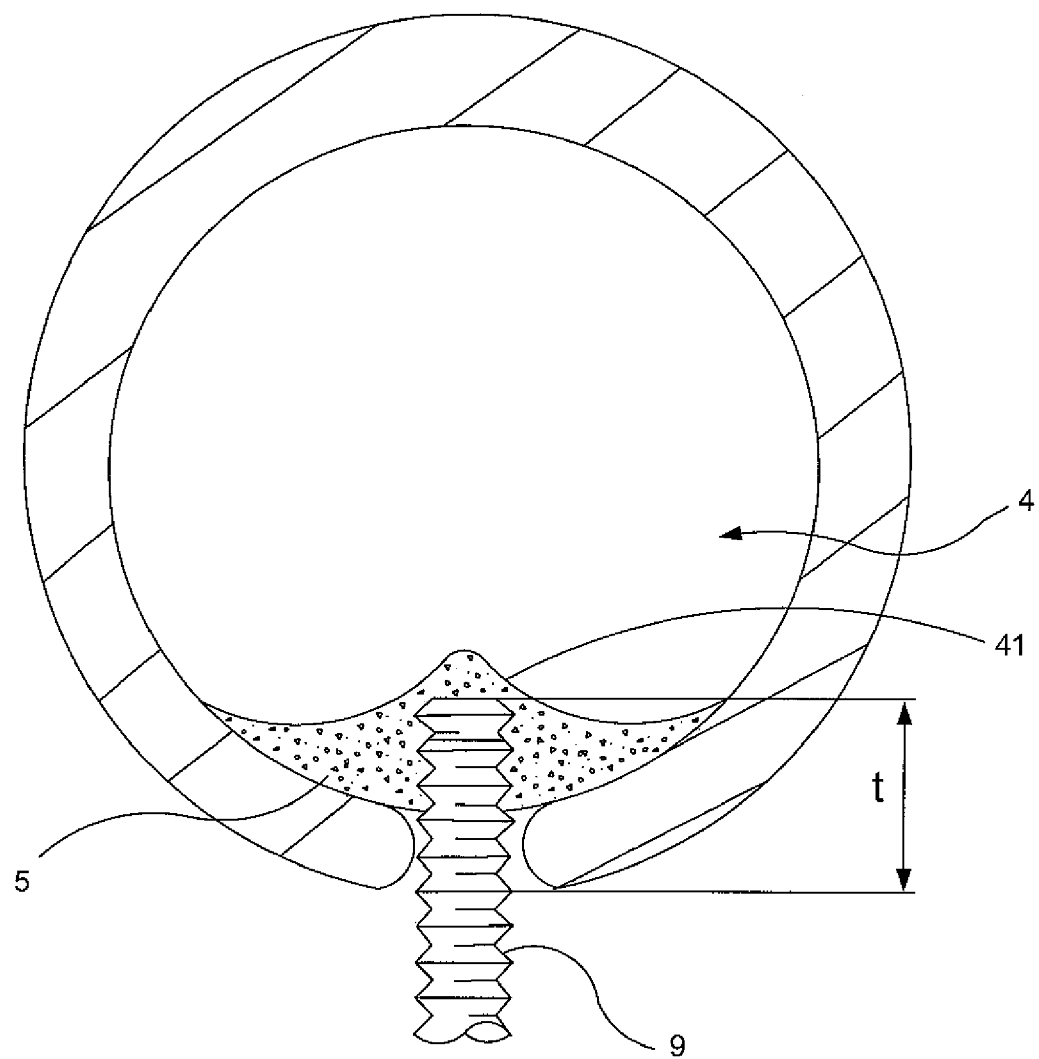
FIG. 3 is a schematic drawing showing the sinus membrane lifted and filled with bone graft, and an implant installed in the sinus according to the present invention.

After filling of bone graft 5 in the space inside the maxillary sinus 4, a prepared implant 9 may be installed as shown in FIG. 3. As the bone graft composition will form bone connected to the cortical bone, a root of implant 9 may be inserted into a relatively deeper distance t, for example about 8 mm, assuring high stability of the installed implant 9 for further installation of a support and tooth crown.

There may be multiple levels of perforation severity. The choice of a sinus correction technique may be made according to the level of perforation severity. For example, perforation severity may be separated 5 classes, with corresponding management techniques.

For example, tooth loss in the posterior area of the maxilla will result in the atrophying of bone along the alveolar ridge over time. This can make implant placement in that area unlikely without first re-establishing a sufficient bone height. A previous approach to this condition involves a lateral window "sinus lift." The advent of a crestal approach based sinus lift method has produced ways to perform a sinus lift with fewer complications, less trauma, and a shorter healing time than a lateral window. There are currently two principle techniques of penetrating crestal bone in order to reach sinus membrane. One is cracking the crestal bone, known as the osteotomy technique. The other technique is to drill through the crestal bone using a hydraulic sinus condensing technique. Once through the crestal bone there are multiple modifications for dissecting the sinus membrane. These methods use a variety of tools and materials such as: bone, sinus elevators, balloon, collagen, sinus condensers, sinus curettes and osteotomy. Sinus membrane perforation is a potential obstacle that must be avoided or managed while performing any type of sinus augmentation procedure, whether through crestal access or lateral access.

Whether preexisting, or created during a procedure, a sinus perforation can cause short and long term complications and should be dealt with quickly. By classifying the perforations, a set of rules may be generated to follow when performing these procedures according to the level of perforation. This in turn allows a dental practitioner to identify and execute the tailored procedure to promote the healing of the sinus membrane and the overall health of a patient. In the current example, classification of sinus membrane perforations will be made primarily by size and degree of separation of soft and hard tissues. Perforations may be separated into 5 classes, each with their own severity and repair procedures.

In class 1 perforations, a practitioner may continue with bone grafting without requiring special procedures. For example, a class 1 perforation may be defined as less than 2 mm in length which is not typically a cause for concern. In a class 1 perforation as defined in the current example, a practitioner may continue with a bone graft and implant placement, but should exercise care not to enlarge the perforation. At this level of perforation, by raising and overlapping the sinus over itself, the perforation should heal with virtually no repercussions.

In a class 2 perforation, a sinus membrane overlapping technique may be used. According to the current example, a class 2 perforation involves a perforation larger than 2 mm but smaller than 5 mm. A class 2 perforation may be corrected without postponing bone grafting or placing of an implant. This type of perforation is most commonly created during a traumatic extraction or while lifting a sinus and may occur with patients having a very thin mucosa. To correct a class 2 perforation, a practitioner may gently dissect approximately 5 to 10 mm of membrane from around the edges of cortical bone. Once this has been accomplished, the membrane can be overlapped in on itself while gently elevating it. After overlapping the membrane in on itself and gently elevating it, bone grafting material may be placed inside the sinus membrane space. Using bone grafting material to compact the membrane will seal a perforation adequately to allow an implant procedure.

A class 3 perforation may involve a delayed membrane casing technique. According to this example, a class 3 perforation consists of a complete tear of sinus membrane. This magnitude of sinus perforation is usually caused by a tooth extraction or by accidentally puncturing the sinus membrane while performing a sinus lift. With a perforation of this size a practitioner may punch though the cortical bone and into the sinus with a hand drill. This approach creates a uniform hole in the bone which will allow for predictable healing results and a safer re-entry into the sinus membrane space after an osteotomy heals. Next, repairing a class 3 perforation involves closing the perforation site and allows it to heal for approximately 3 weeks to allow gingival tissue to grow in the area of the perforation with granulation tissue in the osteotomy site. Once this tissue has formed, the site can be reopened and a split thickness incision may be made in order to create a flap with including gingival tissue that exposes both the osteotomy and granulation tissue inside. In this way, over the course of 3 weeks sinus membrane or gingival connective tissue should heal and form adjacent to granulation tissue. Then, the sinus membrane may be lifted gently with bone grafting material and an implant may be placed in the sinus membrane space.

While the class 1, 2, and 3 perforations described above are typically encountered and repaired during an original procedure, class 4 and 5 perforations are encountered after a perforation has occurred and typically has attempted to heal. Class 4 and 5 perforations are usually created during extraction complications, or multiple failed sinus lift attempts.

In a class 4 perforation, a split thickness sinus membrane casing technique may be used. Typically, a class 4 perforation exposes a bony antra-oral communication, with only the soft tissue intact. A split thickness sinus membrane casing technique is similar to a "delayed technique" with a difference. In particular, instead of making a final osteotomy and waiting for the osteotomy to heal, a split thickness sinus membrane casing technique involves using the osteotomy site as it has naturally healed. This technique is basically a delayed technique without a delay, and is suitable to correct a sinus membrane that has been perforated long enough for tissue to have grown into the tooth socket or osteotomy. This approach involves making a split thickness incision, creating a gingival tissue flap, and exposing the healed tissue inside. Then, the gingival tissue and sinus membrane may be gently lifted with bone grafting material.

A class 5 perforation usually results from severe extraction complications or multiple perforations resulting from repeated attempts to perform a sinus lift when both cortical bone and gingival tissue do not close while healing. A class 5 perforation may be classified by a complete antra-oral communication ranging in size from a pinhole, to several centimeters in diameter. In class 5 perforations, the gingival tissue will have grown into the opening which will prevent bone or sinus membrane from naturally closing the wound. In order to repair this type of perforation, an "invagination technique" may be used as described with reference to FIG. 1.

Figure 4:
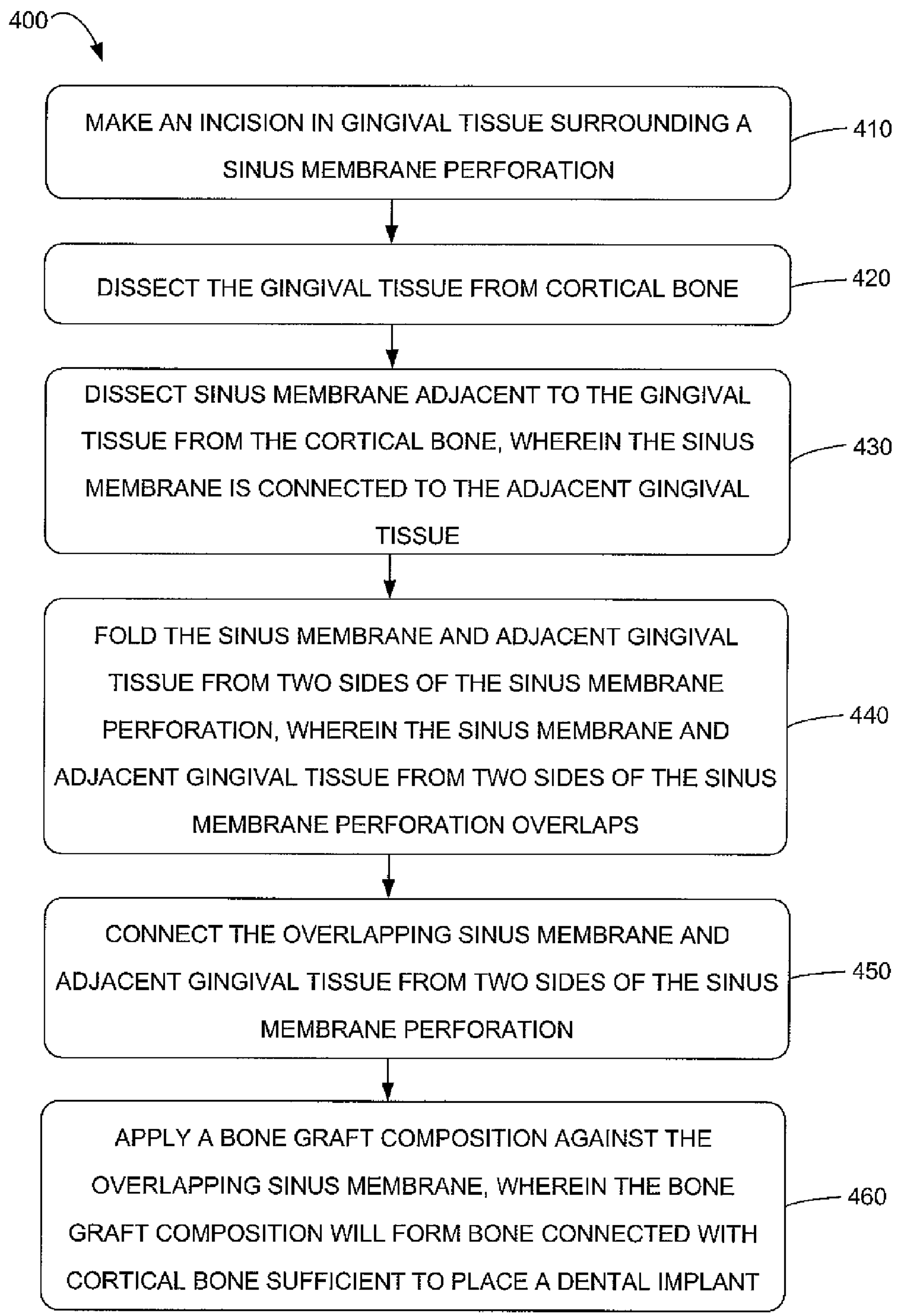
FIG. 4 is a flow diagram showing a sinus correction method.

Continuing with the Figures, FIG. 4 shows a flow diagram of an embodiment of a method 400 for a sinus correction. First, as indicated in block 410, method 400 comprises making an incision in gingival tissue surrounding a sinus membrane perforation.

Method 400 also comprises dissecting the gingival tissue from cortical bone, as indicated in block 420. Next, method 400 comprises dissecting sinus membrane adjacent to the gingival tissue from the cortical bone, wherein the sinus membrane is connected to the adjacent gingival tissue, as indicated at 430.

Method 400 also comprises overlapping the sinus membrane and adjacent gingival tissue from two sides of the sinus membrane perforation, wherein the sinus membrane and adjacent gingival tissue from two sides of the sinus membrane perforation overlaps, as indicated in block 440. Such overlapping of the sinus membrane and applying a bone graft composition may be accomplished by using a dental instrument including a curved end portion for overlapping sinus membrane and a bone graft applicator, for example the dental instrument described with relation to FIG. 2.

In some embodiments, the curved end portion and the bone graft applicator of the dental instrument may be coated with titanium. In yet another embodiment, the curved end portion may have a diameter of 2 mm. In this example, the sinus correction method 400 involves making the incision in gingival tissue approximately 2 mm from the sinus membrane perforation.

Next, method 400 comprises connecting the overlapping sinus membrane and adjacent gingival tissue from two sides of the sinus membrane perforation, as indicated at 450. In some embodiments, the overlapping sinus membrane may be connected by suturing the gingival tissue together from two sides of the sinus membrane perforation.

Then, method 400 comprises applying a bone graft composition adjacent to the overlapping sinus membrane, wherein the bone graft composition forms bone connected with cortical bone sufficient to place a dental implant, as indicated at 460. In some embodiments, applying a bone graft composition may further comprise applying a first spongy bone graft composition adjacent to the sinus membrane; and applying a second particulate bone graft composition.

It will further be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of any of the above-described processes is not necessarily required to achieve the features and/or results of the embodiments described herein, but is provided for ease of illustration and description.

The subject matter of the present disclosure includes all novel and nonobvious combinations and subcombinations of the various processes, systems and configurations, and other features, functions, acts, and/or properties disclosed herein, as well as any and all equivalents thereof. Although particular embodiments have been described in detail for purposes of illustration, various modifications and enhancements may be made without departing from the spirit and scope of the invention as recited by the appended claims.

The invention claimed is:

1. A sinus correction method for treating a sinus membrane perforation, the method comprising the steps of:

identifying the sinus membrane perforation;

making an incision in gingival tissue located adjacent to the sinus membrane perforation;

dissecting the gingival tissue from cortical bone;

dissecting sinus membrane adjacent to the gingival tissue from the cortical bone, wherein the sinus membrane is connected to the adjacent gingival tissue;

overlapping the sinus membrane and adjacent gingival tissue from two sides of the sinus membrane perforation and creating a sinus membrane space between the sinus membrane and the cortical bone, wherein the sinus membrane and adjacent gingival tissue separated from two sides of the sinus membrane perforation are overlapping;

connecting the overlapping sinus membrane and adjacent gingival tissue separated from two sides of the sinus membrane perforation; and inserting a bone graft composition into the sinus membrane space located between the overlapping sinus membrane and the cortical bone, wherein the bone graft composition forms bone connected with cortical bone sufficient to place a dental implant.

2. The sinus correction method of claim 1, wherein connecting the overlapping sinus membrane involves suturing the gingival tissue together from two sides of the sinus membrane perforation.

3. The sinus correction method of claim 1, wherein applying a bone graft composition further comprises: applying a first bone graft composition adjacent to the sinus membrane; and applying a second particulate bone graft composition.

4. The sinus correction method of claim 1, wherein, in the step of overlapping, the sinus membrane is overlapped utilizing a curved end portion of a dental instrument, and, in the step of inserting, the bone graft composition is inserted utilizing a bone graft applicator of the dental instrument, the curved end portion and the bone graft applicator are located on opposing ends of the dental instrument.

5. The sinus correction method of claim 4, wherein the curved end portion and the bone graft applicator are coated with titanium.

6. The sinus correction method of claim 5, where the curved end portion has a diameter of 2 mm.

7. The sinus correction method of claim 1, wherein the incision in gingival tissue is made approximately 2 mm from the sinus membrane perforation.

* * * * *